(12) United States Patent
Kim et al.

(10) Patent No.: US 9,389,059 B2
(45) Date of Patent: Jul. 12, 2016

(54) APPARATUS AND METHOD FOR MEASURING LENGTH OF PIPE

(71) Applicants: Jun-Tae Kim, Seoul (KR); Chi-Sun Ahn, Seoul (KR); Seung-Hwan Jung, Seoul (KR); Sang-Chul Youn, Seoul (KR); Duck-Gu Jeon, Seoul (KR)

(72) Inventors: Jun-Tae Kim, Seoul (KR); Chi-Sun Ahn, Seoul (KR); Seung-Hwan Jung, Seoul (KR); Sang-Chul Youn, Seoul (KR); Duck-Gu Jeon, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 713 days.

(21) Appl. No.: 13/667,667

(22) Filed: Nov. 2, 2012

(65) Prior Publication Data

US 2013/0120007 A1    May 16, 2013

Related U.S. Application Data

(63) Continuation of application No. 12/458,213, filed on Jul. 2, 2009, now Pat. No. 8,326,572.

(30) Foreign Application Priority Data

Sep. 5, 2008    (KR) .................. 10-2008-0087933

(51) Int. Cl.
*G01B 7/02* (2006.01)
*G01D 5/165* (2006.01)
*G01N 27/04* (2006.01)
*H01L 21/66* (2006.01)

(52) U.S. Cl.
CPC ........ *G01B 7/02* (2013.01); *G01D 5/165* (2013.01); *G01N 27/041* (2013.01); *H01L 22/34* (2013.01)

(58) Field of Classification Search
CPC ........... G01D 5/165; H01L 2924/0002; G01N 27/041; G01B 7/02
USPC ............................ 324/699, 635, 716; 367/13
See application file for complete search history.

(56) References Cited

U.S. PATENT DOCUMENTS

| | | | | |
|---|---|---|---|---|
| 4,101,827 A | * | 7/1978 | Offner | G01M 3/18 324/559 |
| 4,195,530 A | * | 4/1980 | Ross | G01N 29/26 73/638 |
| 4,234,942 A | | 11/1980 | Prause et al. | |
| 4,241,430 A | | 12/1980 | Kayem et al. | |

(Continued)

FOREIGN PATENT DOCUMENTS

| | | |
|---|---|---|
| DE | 10 2004 056069 | 5/2006 |
| EP | 0 160 356 | 11/1985 |
| JP | 7-198306 A | 8/1995 |

(Continued)

*Primary Examiner* — Jermele M Hollington
*Assistant Examiner* — Christopher McAndrew
(74) *Attorney, Agent, or Firm* — Dentons US LLP

(57) ABSTRACT

An apparatus for detecting a pipe length in an air conditioning system includes a detector to detect a signal traveled through a pipe; and a processor to determine a pipe length based on the detected signal.

18 Claims, 5 Drawing Sheets

(56) References Cited

U.S. PATENT DOCUMENTS

| | | | |
|---|---|---|---|
| 4,393,711 A * | 7/1983 | Lapides | G01H 1/00 73/1.82 |
| 4,429,743 A * | 2/1984 | Bodine | E21B 28/00 166/177.1 |
| 4,471,294 A * | 9/1984 | Nielsen | G01R 31/08 324/534 |
| 4,584,676 A * | 4/1986 | Newman | G01B 17/00 367/108 |
| 4,852,407 A | 8/1989 | Komine et al. | |
| 4,930,350 A | 6/1990 | Bode et al. | |
| 4,935,884 A * | 6/1990 | Hajicek | G01B 17/00 367/127 |
| 5,530,357 A * | 6/1996 | Cosman | G01V 3/15 324/326 |
| 5,640,092 A * | 6/1997 | Motazed | G01V 3/104 324/247 |
| 6,108,268 A * | 8/2000 | Moss | E21B 17/00 175/56 |
| 2002/0016160 A1 | 2/2002 | Ishikawa et al. | |
| 2006/0151179 A1* | 7/2006 | Boyadjieff | E21B 17/003 166/380 |

FOREIGN PATENT DOCUMENTS

| KR | 20-1998-0062839 | 11/1998 |
|---|---|---|
| KR | 10-2007-0013540 A | 1/2007 |

* cited by examiner

| STRENGTH OF RECEIVED SIGNAL | IMPEDANCE OF IMPEDANCE COUPLING PORTION | . . . | PIPE LENGTH |
|---|---|---|---|
| . . . | . . . | . . . | . . . |
| 3.00V | 30μH | | 10m |
| 3.10V | 30μH | | 15m |
| . . . | . . . | . . . | . . . |
| . . . | . . . | . . . | . . . |

APPARATUS AND METHOD FOR MEASURING LENGTH OF PIPE

RELATED APPLICATION

This application is a Continuation of application Ser. No. 12/458,213, filed on Jul. 2, 2009, which claims the benefit of Korean Application No. 10-2008-0087933, filed on Sep. 5, 2008, which is herein expressly incorporated by reference in its entirety.

BACKGROUND

1. Field of the Disclosure

The present disclosure relates to an apparatus and method for measuring a length of a pipe of an air conditioning system with indoor unit and outdoor unit, and particularly, to an apparatus and method for measuring a length of a pipe of an air conditioning system by measuring a strength of a length detection signal sent from one end of the pipe.

2. Background

In general, an air conditioner includes an outdoor unit installed outdoors, and an indoor unit installed indoors, and a connection pipe for transferring refrigerant, which is disposed between the outdoor unit and the indoor unit.

As such, in the air conditioner, the connection pipe disposed between the outdoor unit and the indoor unit is long in length, and the indoor unit and the outdoor unit are installed, respectively, inside and outside a building. Usually, most of the connection pipe is placed inside the building.

When the connection pipe for connecting the indoor unit and the outdoor unit to each other is long and placed inside the building, an accurate length of the connection pipe needs to be known in order to fill or charge the refrigerant.

In case of injecting or filling the refrigerant in the related art air conditioning system, the length of the refrigerant pipe, which should be known in order to measure an exact amount of injected refrigerant, cannot be measured accurately.

In addition, in case where a manager of the air conditioning system cannot physically measure the length of pipe because the pipe installed between the indoor and outdoor units of the air conditioning system is not exposed outwardly to due to a structure of the building in which the air conditioning system is installed, it is inconvenient to measure the length of the pipe, and also excessive costs are required for maintenance thereof.

SUMMARY

Therefore, it is desirable to provide a pipe length detecting apparatus in an air conditioning system, which is directed to preventing a malfunction of the air conditioning system or degradation of air conditioning capability thereof due to the lack of refrigerant, by easily accurately measuring the length of a refrigerant pipe installed between indoor and outdoor units of the air conditioning system, and accordingly supplying an appropriate amount of refrigerant.

Also, it is desirable to provide a pipe length measuring apparatus in an air conditioning system, which is directed to providing convenience to a user or manager and additionally reducing a maintenance cost, by allowing the pipe length to be easily measured by a simple operation or installation even in case where a manager of the air conditioning system cannot physically measure the length of pipe because the pipe installed between the indoor and outdoor units of the air conditioning system is not exposed outwardly due to a structure of the building in which the air conditioning system is installed.

To achieve these and other advantages and in accordance with the purpose of the present invention, as embodied and broadly described herein, there is provided an apparatus for detecting a pipe length in an air conditioning system including a detector to detect a signal traveled through a pipe; and a to processor to determine a pipe length based on the detected signal.

In another aspect of the present invention, an apparatus for detecting a pipe length may include a first impedance coupler to couple to a pipe; a signal generator to generate a signal to be sent to the pipe through the first impedance coupler; a second impedance coupler to couple to the pipe; a detector coupled to the second impedance coupler to detect the signal traveled through the pipe from the first impedance coupler to the second impedance coupler; and a processor that determines a length of the pipe based on a difference in amplitude of the sent signal and the detected signal, and the impedances of the first and second coupling portions.

The foregoing and other objects, features, aspects and advantages of the embodiments of the present invention will become more apparent from the following detailed description when taken in conjunction with the accompanying drawings.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION

Description will now be given in detail of a pipe length detecting apparatus in an air conditioning system in accordance with one embodiment of the present invention, with reference to FIGS. 1 to 4.

Figure 1:
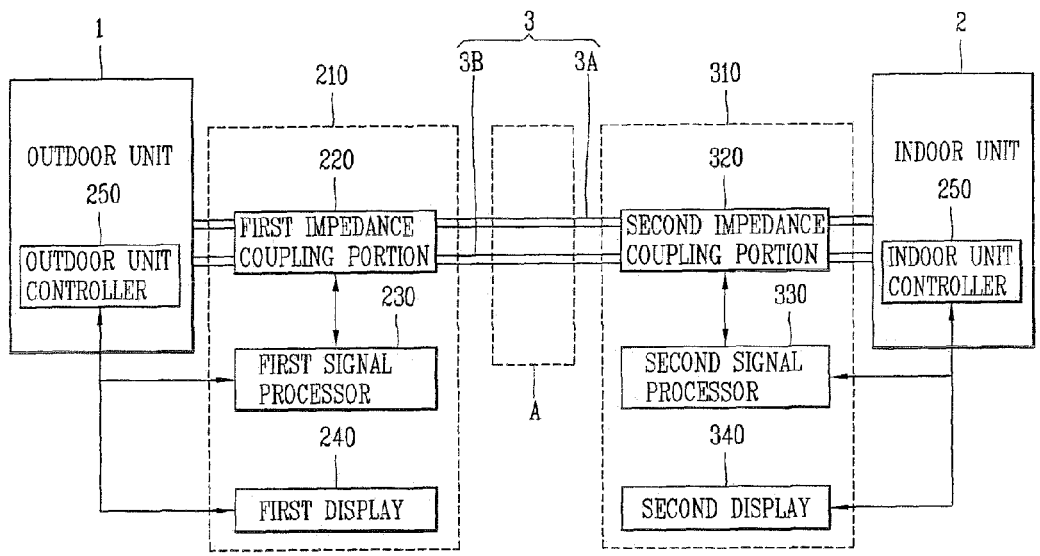
FIG. 1 is a block diagram showing a pipe length detecting apparatus for measuring a length of a refrigerant pipe of an air conditioning system in accordance with one embodiment of the present invention.
Figure 2A:
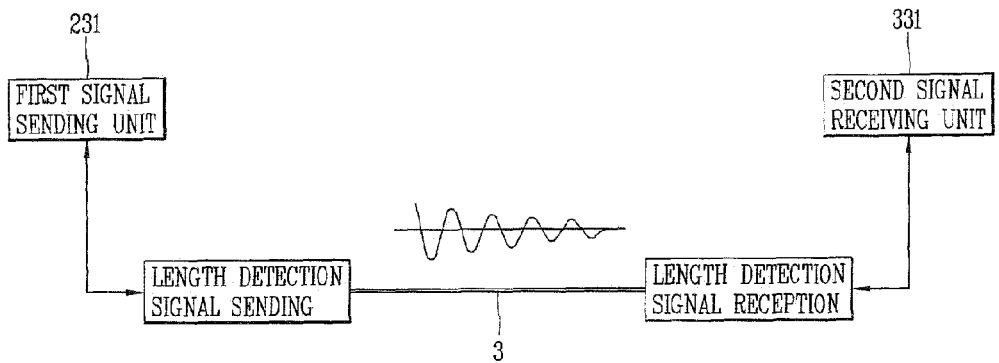
FIG. 2(a) shows a case of detecting the length of the refrigerant pipe by sending a length detection signal from an outdoor unit side and receiving such signal at an indoor unit side.
Figure 2B:
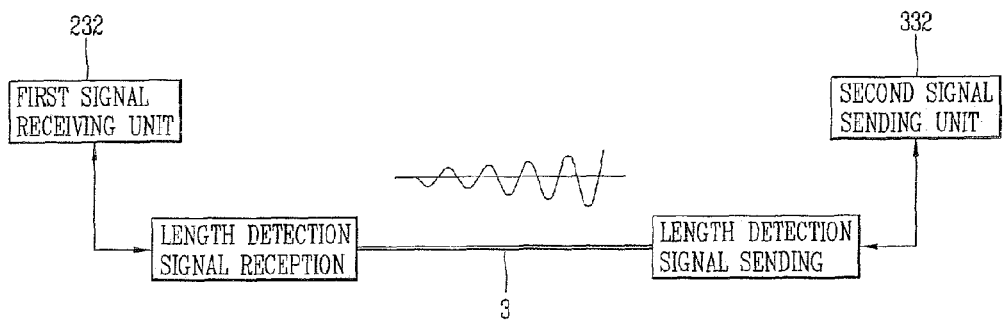
FIG. 2(b) shows a case of detecting the length of the refrigerant pipe by sending the length detection signal from the indoor unit side and receiving such signal at the outdoor unit side.

FIG. 1 is a block diagram showing a pipe length detecting apparatus for measuring a length of a refrigerant pipe of an air conditioning system in accordance with one embodiment of the present invention, FIG. 2(a) shows a case of detecting the length of the refrigerant pipe by sending a length detection signal from an outdoor unit side 231 and receiving such signal at an indoor unit side 331, and FIG. 2(b) shows a case of detecting the length of the refrigerant pipe by sending the length detection signal from the indoor unit side 332 and receiving such signal at the outdoor unit side 232.

Figure 3A:
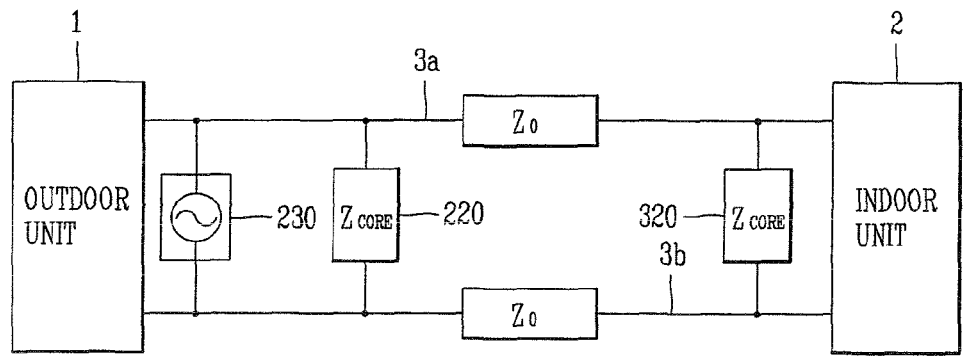
FIGS. 3(a) and 3(b) are equivalent circuit views of the refrigerant pipe length detecting apparatus in an air conditioning system in accordance with the embodiment of the present invention shown in FIGS. 2(a) and 2(b)
Figure 3B:
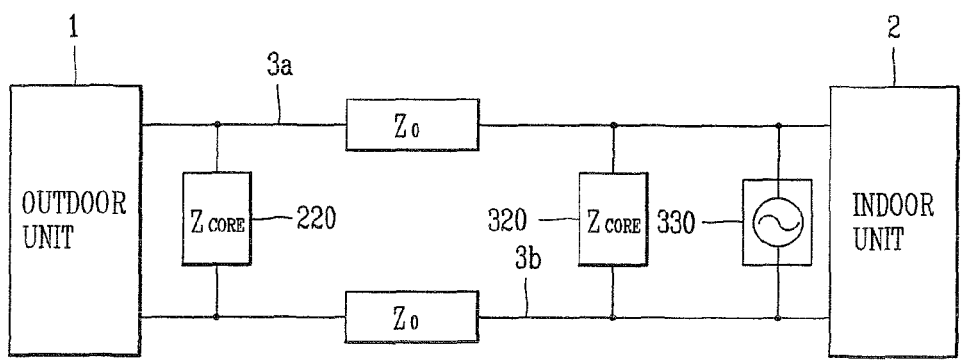
Figure 4:
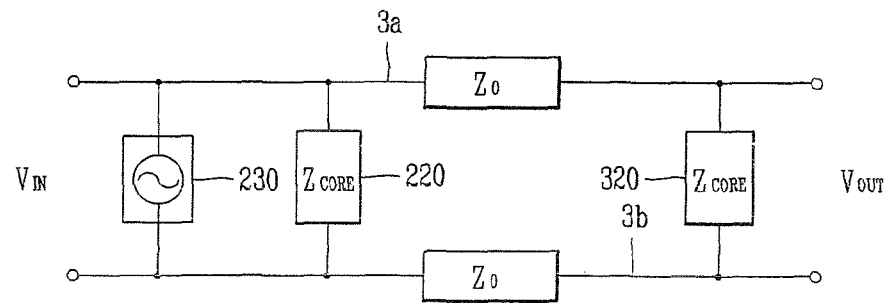
FIG. 4 is an equivalent circuit view for a case of calculating a voltage applied to a length detecting unit of an indoor unit side in the equivalent circuit shown in FIG. 3(a)

FIGS. 3(a) and 3(b) are equivalent circuit views of the refrigerant pipe length detecting apparatus in an air conditioning system in accordance with the embodiment of the present invention shown in FIGS. 2(a) and 2(b), and FIG. 4 is an equivalent circuit view for a case of calculating a voltage applied to a length detecting unit of an indoor unit side in the equivalent circuit shown in FIG. 3(a).

As shown in FIGS. 1 to 4, a pipe length detecting apparatus according to the embodiment of the present invention, in an air conditioning system with indoor unit and outdoor unit, may include a first length detecting unit 210 coupled to one end of a refrigerant pipe disposed between the indoor and outdoor units 2 and 1 to send a length detection signal via the refrigerant pipe, and a second length detecting unit 310 coupled to another end of the refrigerant pipe to receive the sent length detection signal and measure an amplitude thereof so as to calculate the length of the pipe.

With such configuration, the refrigerant pipe is used as a transfer path of the length detection signal, and accordingly the length of the pipe between the indoor and outdoor units 2 and 1, the length being used for measuring an amount of refrigerant, can automatically be detected.

The first length detecting unit 210 may include a first impedance coupling portion 220 coupled to one end of the refrigerant pipe to allow the length detection signal to be sent to the refrigerant pipe, and a first signal processor 230 for sending the length detection signal to the refrigerant pipe via the first impedance coupling portion 220.

The second length detecting unit 310 may include a second signal processor 330 for detecting an amplitude of the received length detection signal so as to calculate the length of the refrigerant pipe, and a second impedance coupling portion 320 coupled to another end of the refrigerant pipe to allow the length detection signal to be sent from the refrigerant pipe to the second signal processor 330.

The first and second impedance coupling portions 220 and 320 may configure an electric loop such that each of the first and second length detecting units 210 and 310 can send and receive the length detection signal as an electric signal via the refrigerant pipe. The second impedance coupling portion 320 of a receiving side can measure a strength of the sent length detection signal.

The first signal processor 230 can also detect a strength of the received length detection signal to measure the length of the refrigerant pipe. The second signal processor 330 can generate a length detection signal to send via the refrigerant pipe.

With such configuration, a user or manager can make the length detection signal sent or received at any side of the indoor unit 2 or the outdoor unit 1, thereby providing convenience of management to the user or manager.

The first and second impedance coupling portions 220 and 320 may be impedance-matched with the refrigerant pipe 3a and 3b, so as to detect a strength of the length detection signal, and may be coupled to the refrigerant pipe at portions corresponding to one-fourth or half of the wavelength of the length detection signal from an end of the refrigerant pipe 3a and 3b.

Also, the first and second impedance coupling portions 220 and 320 may be formed of a magnetic substance. Such magnetic substance can minimize an attenuation of a signal due to each impedance coupling portion 220 and 320.

The first and second length detecting units 210 and 310 may respectively further include first and second refrigerant pipe length displays 240 and 340 for visually displaying information related to the detected refrigerant pipe length, which allows a user or manager to be known of the refrigerant pipe length or other operational states sensed by controllers 250 and 350 of the indoor and outdoor units 2 and 1.

Preferably, the first length detecting unit 210 is disposed at the side of the outdoor unit 1, and the second length detecting unit 310 is disposed at the side of the indoor unit 2.

Each of the first and second length detecting units 210 and 310 may be detachably coupled to the refrigerant pipe, and there may be at least one or more of the first and second length detecting units 210 and 310, respectively. With such configuration, a user or manager can easily measure the refrigerant pipe length at a random position.

Hence, such information related to the detected refrigerant pipe length is calculated at the side of the indoor unit 2 via the refrigerant pipe disposed between the outdoor and indoor units 2 and 1 so as to be collected at the side of the outdoor unit 1. Each of the displays 240 and 340 displays each refrigerant pipe length of plural indoor units.

In this embodiment, the first and second length detecting units 210 and 310 are controlled by the controllers 250 and 350 of the outdoor and indoor units 1 and 2, respectively, and in an alternative embodiment, a separate controller may be included.

Hereinafter, description will be given in detail of a method for calculating a pipe length by using an electric equivalent circuit of the outdoor and indoor units 1 and 2, the refrigerant pipe 3 and the magnetic impedance coupling portions 220 and 320 of the pipe length detecting apparatus according to an embodiment of the present invention as shown in FIG. 4.

Upon flowing an alternating current (AC) signal in a refrigerant pipe disposed between the outdoor and indoor units 1 and 2, the AC signal is characteristically attenuated depending on the length of the refrigerant pipe due to an impedance $Z_o$ of the pipe itself as a transfer path.

The impedance $Z_o$ of the pipe is in proportion to the length. The strength of the AC signal used for detecting the length of the refrigerant pipe is attenuated by the impedance $Z_o$ of the pipe and the impedance coupling portions ($Z_{core}$) 220 and 320.

That is, once an impedance value of the impedance coupling portion and a strength of an AC control signal of sending/receiving end are known, length information can be obtained in an inverse manner.

$$Z_o = \sqrt{\frac{Z}{Y}} = \sqrt{\frac{R_o + jwL_o}{G_o + jwC_o}} \quad (w = 2\pi f) \qquad \text{[Equation 1]}$$

The transfer path impedance is composed of resistance R, inductance L, capacitance C and conductance G.

According to the results of Equation 1, elements R and G may be ignored is due to jwL>>R and jwC>>G in an actual refrigerant pipe. That is, it can be noticed that most of elements of the length detection signal are not lost, and Equation 1 can be approximated like Equation 2

$$Z_o = \sqrt{\frac{jwL_o}{jwC_o}} = \sqrt{\frac{L_o}{C_o}} \quad \text{[Equation 2]}$$

As can be seen in the results of Equation 2, Z0 is in proportion to a length so as to be represented by a function with respect to the length.

$$Z_o = f(d), \, d = \text{length}$$

For implementing the first and second impedance coupling portions 220 and 320 using a magnetic substance, the impedance $Z_{core}$ of each of the first and second impedance coupling portions 220 and 320 is only composed of the element L, which is represented by Equation 3.

$$Z_{core} = jwL_{core}(w=2\pi f) \quad \text{[Equation 3]}$$

Therefore, upon calculating the strength of the received length detection signal using the equivalent circuit shown in FIG. 4, it can be represented by Equation 4.

$$V_{out} = V_{in} \times \frac{Z_{core}}{Z_{core} + 2Z_0} = V_{in} \times \frac{jwL_{core}}{jwL_{core} + 2f(d)} \quad \text{[Equation 4]}$$

The above Equation 4 can be represented by a metric function like Equation 5.

$$f(d) = \frac{jwL_{core}}{2} \times \left(\frac{V_{in}}{V_{out}} - 1\right) \quad \text{[Equation 5]}$$

The length of the refrigerant pipe calculated according to the embodiment of the present invention can thusly be represented by Equation 6.

$$d = f^{-1}\left\{\frac{jwL_{core}}{2} \times \left(\frac{V_{in}}{V_{out}} - 1\right)\right\} \quad \text{[Equation 6]}$$

Hereinafter, a method for detecting a refrigerant pipe length in an air conditioning system in accordance with one embodiment of the present invention will be described with reference to FIGS. 5 to 7.

Figure 6:
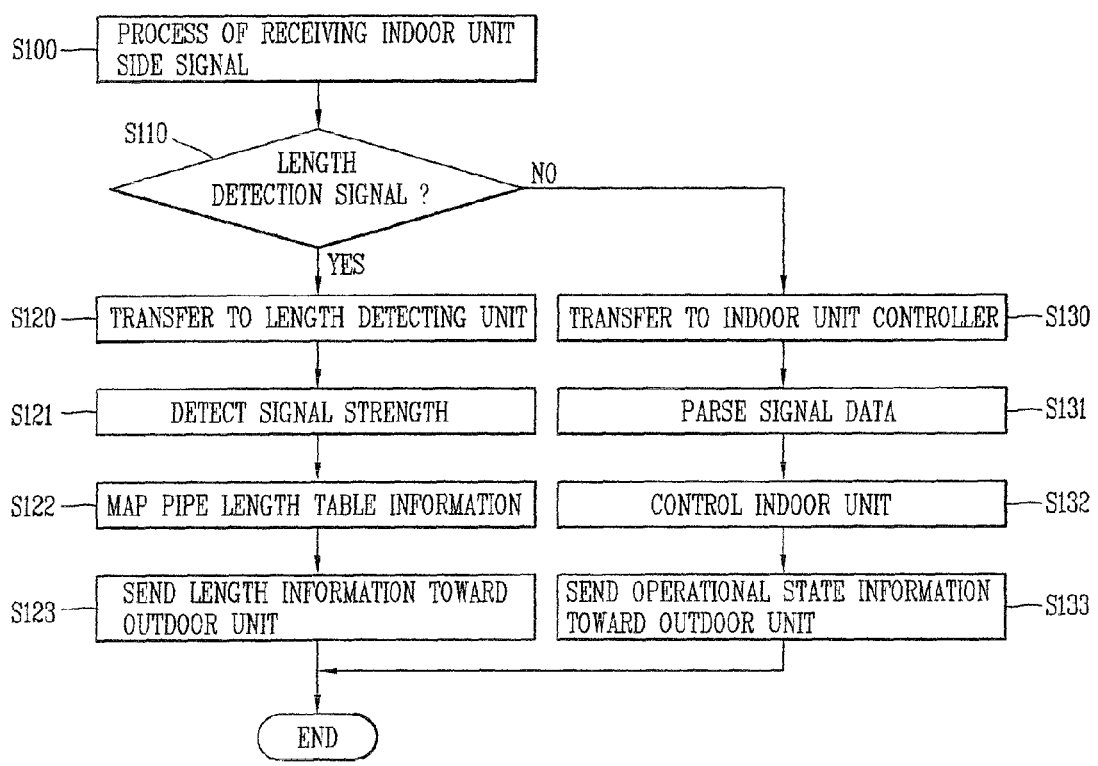
FIG. 6 is a flowchart of an exemplary process of calculating a length of the refrigerant pipe by receiving a length detection signal from an indoor unit side.
Figures 7, 8:
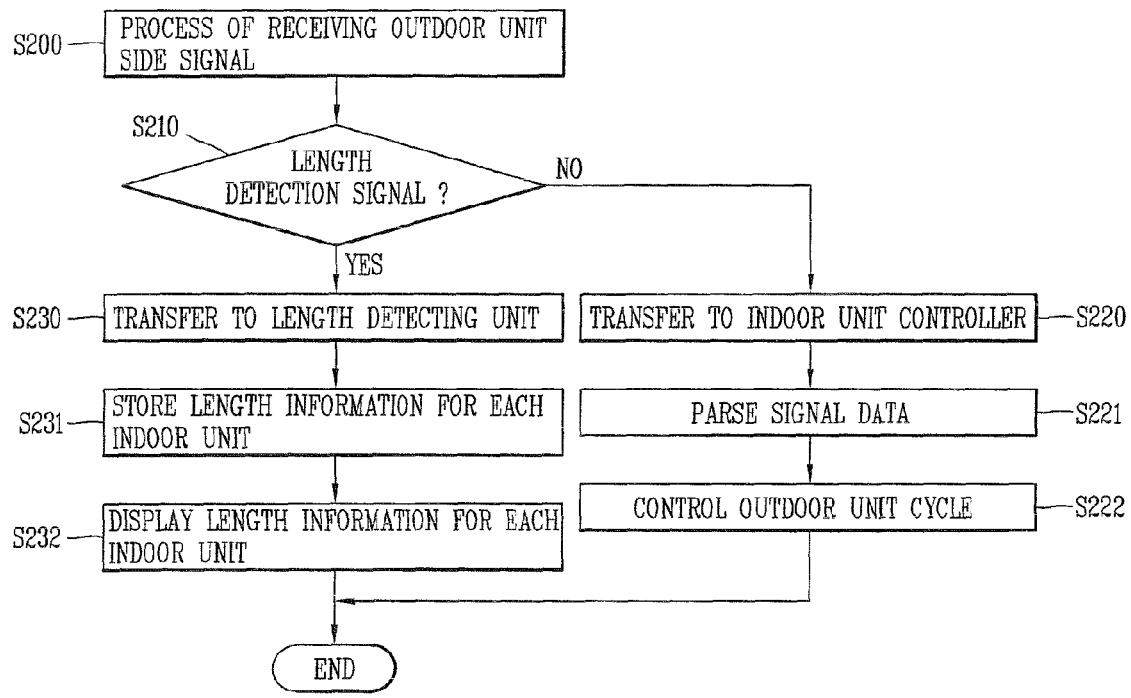
FIG. 7 is a flowchart of an exemplary process of receiving and displaying, at an outdoor unit side, refrigerant pipe length information calculated at the indoor unit side.
FIG. 8 is an exemplary data table showing pipe lengths according to a strength of a length detection signal, which is sent via the pipe and received at a receiving side.

FIG. 6 is a flowchart of a process of calculating a length of the refrigerant pipe by receiving a length detection signal from an indoor unit side, FIG. 7 is a flowchart of a process of receiving and displaying, at an outdoor unit side, refrigerant pipe length information calculated at the indoor unit side, and FIG. 8 is a data table showing pipe lengths according to a strength of a length detection signal, which is sent via the pipe and received at a receiving side.

Figure 5:
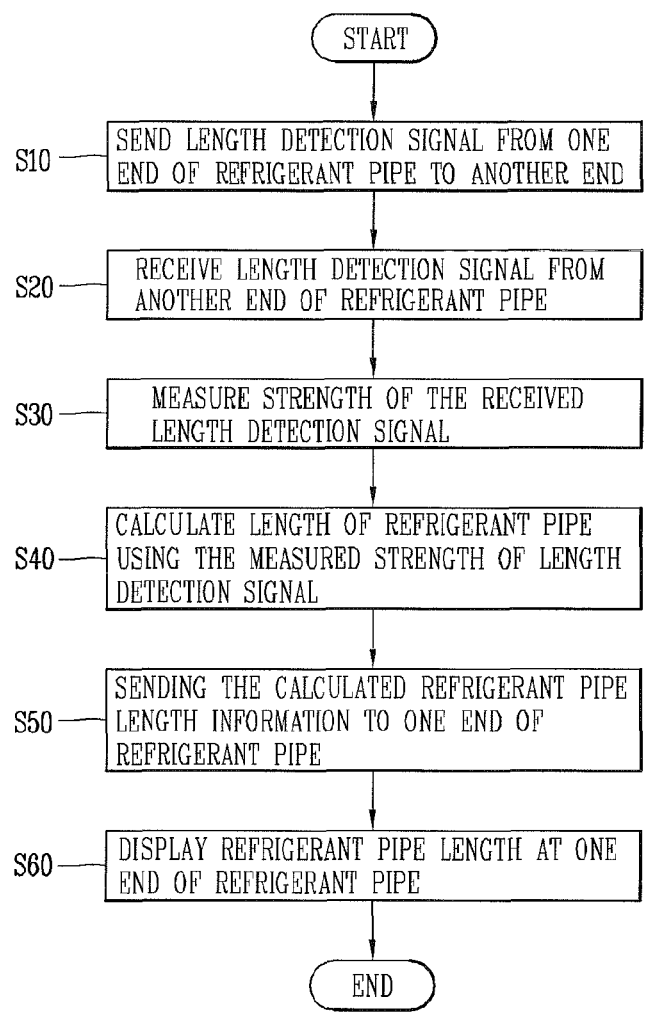
FIG. 5 is a flowchart showing an exemplary method for detecting a length of a refrigerant pipe of an air conditioning system in accordance with one embodiment of the present invention.

As shown in FIGS. 5 to 7, a method for detecting a refrigerant pipe length in accordance with one embodiment of the present invention may include sending a length detection signal from one end of a refrigerant pipe disposed between indoor and outdoor units of an air conditioning system (S10), receiving the sent length detection signal so as to measure a strength of the received length detection signal (S20 and S30), and calculating the length of the refrigerant by using the measured strength of the received length detection signal and a strength of the length detection signal upon being sent (S40).

Preferably, the length detection signal sent in the detection signal sending step S10 is a sine wave (sinusoidal wave) with a single frequency within a band of several hundreds of KHz. More preferably, the sine wave of the single frequency has a frequency of 100 KHz.

The length calculating step S40 is implemented by calculating the length of the pipe using a preset impedance value of the refrigerant pipe, an impedance value of the impedance coupling portion, a strength of a length detection signal upon being sent, and a strength of a length detection signal detected at a receiving side. Such information related to the calculated length of the refrigerant pipe is then sent toward the outdoor unit (S50).

The detection method may further include displaying the detected length of the refrigerant pipe (S60).

As shown in FIGS. 6 and 7, the method for detecting the pipe length according to the one embodiment of the present invention can also be implemented so as to send and receive information for controlling the indoor and outdoor units as well as the length detection signal.

That is, during a process (S100) of receiving a signal at the side of an indoor unit, after receiving the signal, the second length detecting unit determines whether the received signal is either a control signal or a length detection signal (S110). The length detection signal is a sine wave with a constant strength while the control signal is a modulated signal, so as to be distinguishable from each other.

If the determined signal is the length detection signal, the second length detecting unit 310 first calculates the strength of the length detection signal and obtains pipe length information based upon a previously prepared data table (S120 to S122). The calculated length information is then sent toward the outdoor unit (S123).

Such data table which shows pipe lengths according to a strength of a length detection signal, which is sent via the pipe and received at a receiving side, is shown in FIG. 8.

On the other hand, the determined signal is the control signal, the indoor unit is controlled according to the control signal (S130 to S133).

That is, during the process (S100) of receiving the signal at the side of the indoor unit, after receiving the signal, the first length detecting unit determines whether the received signal is either a control signal or a length detection signal (S210). If the determined signal is the length detection signal, such length value is displayed at the side of the outdoor unit (S230 to S232). On the other hand, if the detected signal is the control signal, then the cycle of the outdoor unit is controlled (S220 to S222).

The pipe length detecting apparatus in an air conditioning system according to an embodiment of the present invention may prevent the malfunction of the air conditioning system or the degradation of air conditioning capability of the air conditioning system, by accurately measuring the length of the refrigerant pipe disposed between indoor and outdoor units of the air conditioning system and accordingly supplying an appropriate amount of refrigerant.

In addition, the pipe length detecting apparatus in an air conditioning system according to an embodiment of the present invention may provide convenience to a user or manager and additionally reduce maintenance cost, by allowing the pipe length to be easily measured by a simple operation or installation even in case where a manager of the air conditioning system cannot physically measure the length of pipe because the pipe installed between the indoor and outdoor units of the air conditioning system is not exposed outwardly due to a structure of the building in which the air conditioning system is installed.

As described above, the present disclosure has described in detail the measurement of a length of a refrigerant pipe disposed between indoor and outdoor units of an air conditioning system with reference to the embodiments and the accompanying drawings. However, such description can be applied to measuring a pipe length in various types of systems and apparatuses having such pipe with an electric conductivity.

The foregoing embodiments and advantages are merely exemplary and are not to be construed as limiting the present disclosure. The present teachings can be readily applied to other types of apparatuses. This description is intended to be illustrative, and not to limit the scope of the claims. Many alternatives, modifications, and variations will be apparent to those skilled in the art. The features, structures, methods, and other characteristics of the exemplary embodiments described herein may be combined in various ways to obtain additional and/or alternative exemplary embodiments.

As the present features may be embodied in several forms without departing from the characteristics thereof, it should also be understood that the above-described embodiments are not limited by any of the details of the to foregoing description, unless otherwise specified, but rather should be construed broadly within its scope as defined in the appended claims, and therefore all changes and modifications that fall within the metes and bounds of the claims, or equivalents of such metes and bounds are therefore intended to be embraced by the appended claims.

What is claimed is:

1. A pipe length detecting apparatus comprising:
   a detector to detect an alternating current (AC) signal traveled through a pipe; and
   a processor to determine a length of the pipe,
   the apparatus further comprising:
   a signal generator to generate the alternating current (AC) signal to be sent through the pipe,
   wherein the alternating current (AC) signal is sent from one end of the pipe to another end of the pipe, and
   wherein the processor determines the length of the pipe based on the detected signal, which is a non-reflected signal.

2. The apparatus of claim 1, further comprising a first impedance coupler that couples to one end of the pipe, wherein the detector detects the alternating current (AC) signal traveled through the pipe at the first impedance coupler.

3. The apparatus of claim 2, further comprising a second impedance coupler that couples to another end of the pipe, wherein the signal generator sends the alternating current (AC) signal to the pipe through the second impedance coupler.

4. The apparatus of claim 3, wherein at least one of the first and second impedance couplers is impedance-matched with the pipe.

5. The apparatus of claim 3, wherein at least one of the first and second impedance couplers is made of a magnetic substance.

6. The apparatus of claim 3, wherein at least one of the first and second impedance couplers is matched to the pipe corresponding to one-fourth or one-half of a wavelength of the alternating current (AC) signal.

7. The apparatus of claim 1, further comprising a display to visually display information related to the length of the pipe.

8. The apparatus of claim 1, further comprising a look-up table stored in a memory, wherein the processor determines the length of the pipe using the look-up table.

9. A pipe length detecting apparatus comprising:
   a first impedance coupler to couple to one end of a pipe;
   a signal generator to generate a signal to be sent to the pipe through the first impedance coupler;
   a second impedance coupler to couple to the pipe;
   a detector coupled to the second impedance coupler to detect the signal traveled through the pipe from the first impedance coupler to the second impedance coupler; and
   a processor that determines a length of the pipe based on a difference in amplitude of the sent signal and the detected signal, and impedances of the first and second impedance couplers,
   wherein the signal generator generates an alternating current (AC) signal,
   wherein the alternating current (AC) signal is sent from one end of the pipe to opposite end of the pipe,
   wherein the detected signal is a non-reflected signal.

10. The apparatus of claim 9, wherein at least one of the first and second impedance couplers is impedance-matched with the pipe.

11. The apparatus of claim 9, wherein at least one of the first and second impedance couplers is made of a magnetic substance.

12. The apparatus of claim 9, wherein at least one of the first and second impedance couplers is matched to the pipe at portions corresponding to one-fourth or one-half of a wavelength of the signal.

13. The apparatus of claim 9, further comprising a display to visually display information related to the pipe length.

14. The apparatus of claim 9, further comprising a look-up table stored in a memory, wherein the processor determines the pipe length using the look-up table.

15. A pipe length detecting apparatus, comprising:
   a detector to detect an alternating current (AC) signal traveled through a pipe;
   a first impedance coupler that couples to one end of the pipe, wherein the detector detects the alternating current (AC) signal traveled through the pipe at the first impedance coupler;
   a signal generator to generate the alternating current (AC) signal to be sent through the pipe; and
   a second impedance coupler that couples to another end of the pipe, wherein the signal generator sends the alternating current (AC) signal to the pipe through the second impedance coupler; and
   a processor to determine a length of the pipe by comparing an amplitude of the detected signal with that of the sent signal,
   wherein the alternating current (AC) signal is sent from one end of the pipe to opposite end of the pipe,
   wherein the detected signal is a non-reflected signal.

16. The apparatus of claim 15, wherein at least one of the first and second impedance couplers is impedance-matched with the pipe.

17. The apparatus of claim 15, wherein at least one of the first and second impedance couplers is made of a magnetic substance.

18. The apparatus of claim 15, wherein at least one of the first and second impedance couplers is matched to the pipe corresponding to one-fourth or one-half of a wavelength of the alternating current (AC) signal.

* * * * *